United States Patent [19]

United States Patent [19]

Beaupre et al.

[11] Patent Number: 4,995,888
[45] Date of Patent: Feb. 26, 1991

[54] SEPARATION OF GAS FROM SOLVENT BY MEMBRANE TECHNOLOGY

[75] Inventors: Richard F. Beaupre, Darien, Conn.; Dick Y. Jung, Fishkill, N.Y.

[73] Assignee: Texaco Inc., White Plains, N.Y.

[21] Appl. No.: 214,983

[22] Filed: Jul. 5, 1988

[51] Int. Cl.$^5$ .................. B01D 53/22; B01D 71/16
[52] U.S. Cl. ................................ 55/16; 55/68; 55/70; 55/73; 423/229
[58] Field of Search ............... 55/16, 48, 68, 73, 158, 55/159, 70; 423/226, 228, 229

[56] References Cited

U.S. PATENT DOCUMENTS

| | | | |
|---|---|---|---|
| 2,617,493 | 11/1952 | Jones | 55/16 |
| 3,062,905 | 11/1962 | Jennings et al. | 55/16 X |
| 3,342,729 | 9/1967 | Strand | 55/16 X |
| 3,651,616 | 3/1972 | Blanchard et al. | 55/16 |
| 3,651,618 | 3/1972 | Klein et al. | 55/16 |
| 3,751,879 | 8/1973 | Allington | 55/189 X |
| 3,911,080 | 10/1975 | Mehl et al. | 55/16 X |
| 4,119,408 | 10/1978 | Matson | 55/16 X |
| 4,171,017 | 10/1979 | Klass | 55/16 X |
| 4,218,312 | 8/1980 | Perry | 55/16 X |
| 4,325,715 | 4/1982 | Bowman et al. | 55/159 X |
| 4,444,571 | 4/1984 | Matsox | 55/16 |
| 4,466,946 | 8/1984 | Goddin, Jr. et al. | 55/16 X |
| 4,469,495 | 9/1984 | Hiraizumi et al. | 55/159 X |
| 4,516,580 | 5/1985 | Polanyi | 55/158 X |
| 4,516,984 | 5/1985 | Warner et al. | 55/16 |
| 4,523,934 | 6/1985 | Joshua | 55/189 |
| 4,659,343 | 4/1987 | Kelly | 55/16 |
| 4,717,407 | 1/1988 | Choe et al. | 55/158 X |
| 4,750,918 | 6/1988 | Sirkar | 55/16 |

FOREIGN PATENT DOCUMENTS 2907188  8/1979  Fed. Rep. of Germany ........ 55/159

Primary Examiner—Robert Spitzer
Attorney, Agent, or Firm—Robert A. Kulason; James J. O'Loughlin; Carl G. Seutter

[57] ABSTRACT

Hydrogen sulfide is separated from the dimethyl ether of tetraethylene glycol through a membrane of hydrolyzed cellulose.

10 Claims, No Drawings

SEPARATION OF GAS FROM SOLVENT BY MEMBRANE TECHNOLOGY

FIELD OF THE INVENTION

This invention relates to the separation of gas from solvent by membrane technology. More particularly it relates to the use of a membrane to regenerate solvent which has been used to absorb gases.

BACKGROUND OF THE INVENTION

As is well known to those skilled-in-the-art, various gases, typified by carbon dioxide or hydrogen sulfide, may be recovered from gas streams by absorption in a lean liquid such as monoethanolamine in order to rid the gas stream of the component or to recover the gas component as a usable product. The rich liquor so produced in the absorber is passed to a stripper wherein the absorbed gas is stripped from the rich liquor to form gas and lean liquor which latter is commonly recycled to the charge for absorption. The stripping step in which the solvent is regenerated may be carried out may be effected by distillation, steam stripping, inert gas stripping, flashing, etc.

It is an object of this invention to provide a novel process for separating a gas from a liquid. Other objects will be apparent to those skilled in the art.

STATEMENT OF THE INVENTION

In accordance with certain of its aspects, this invention is directed to a method of separating gas from a charge rich liquid containing gas dissolved in solvent therefor which comprises maintaining said charge rich liquid containing gas dissolved in solvent therefor in liquid phase in contact with a gas-permeable, essentially solvent impermeable membrane of pore size of less than about 1000 A and molecular weight cutoff of below about 1000 selected from the group consisting of cellulose acetate membrane, hydrolyzed cellulose membrane, polyethyleneimine membrane, and polytetrafluoroethylene membrane;

maintaining a pressure drop across said gas-permeable essentially solvent-impermeable membrane;

passing said gas from the charge rich liquid containing gas dissolved in solvent therefor at the higher pressure side of said membrane through said membrane to the lower pressure side of said membrane thereby forming lean liquid containing decreased quantities of gas dissolved in solvent on the higher pressure side of said membrane and, on the lower pressure side of said membrane, gas containing decreased quantities of liquid;

recovering lean liquid containing decreased quantities of gas dissolved in solvent from the high pressure side of said membrane; and recovering gas containing decreased quantities of liquid from the lower pressure side of said membrane.

DESCRIPTION OF THE INVENTION

The charge rich liquid containing gas dissolved in solvent may be obtained from various sources including natural liquids or process-derived liquids. The instant method is however particularly adapted to be used with an absorption system in which a charge gas stream is contacted with a lean liquid absorbent which absorbs a component from the gas stream to produce a rich liquor. Although the process of this invention may be used to separate basic gases such as ammonia, commonly the gas is an acidic gas; and it may be desirable to separate this component to remove it from the charge gas stream in which it is an undesirable component; or it may be desirable to recover this component in order to utilize it in another process.

The acidic gases which may be separated by the process of this invention may include:

TABLE

| |
|---|
| carbon dioxide |
| hydrogen sulfide |
| carbon disulfide |
| hydrogen cyanide |
| carbonyl sulfide |
| methyl mercaptan |
| sulfur dioxide |

Liquid absorbents which are illustrative of those which may be utilized in practice of the process of this invention may include those which function as physical solvents (which exhibit substantially no chemical reaction with the gases which are absorbed) or chemical solvents (which exhibit substantial chemical reaction with the gases which are absorbed) or combination physical/chemical solvents which are mixtures of solvents including at least one solvent of each category.

It will be apparent to those skilled in the art that the particular solvent employed may depend on the gas being recovered; and that a solvent which may be a physical solvent for one gas may be a chemical solvent in the presence of another gas.

Typical physical solvents which may be employed may include the following:

TABLE

| |
|---|
| Alcohols |
| methanol |
| ethanol |
| propanols etc. |
| Glycols |
| ethylene glycol |
| propylene glycol |
| butylene glycol etc. |
| Polyoxyalkylene Polyols |
| poly (10) oxyethylene diol |
| poly (15) oxyethylene diol |
| poly (10) oxypropylene diol etc. |
| Glycol Ethers |
| tetraethylene gylcol dimethyl ether |
| pentaethylene gylcol dimethyl ether |
| Organic Carbonates |
| dimethyl carbonate |
| diethyl carbonate etc. |
| Nitrogen Heterocycles |
| N-methyl pyrrolidone |
| N-(3-hydroxypropyl) pyrrolidone |
| 1-methyl-pyrrolidinol-3 |
| N-methyl pyrrolidine etc. |
| Sulfur Heterocycles |
| thiophene |
| tetrahydrothiophene-1,1 dioxide (sulfolane) |
| tetramethylene sulfoxide |
| 3-methyl sulfolane etc. |

Typical chemical solvents which may be employed may include the following:

TABLE

| |
|---|
| Amines |
| aniline |
| N,N-dimethyl aniline |
| N-formyl morpholine |
| Olamines |

TABLE-continued monoethanolamine (MEA)
diethanolamine (DEA)
N-methyl diethanolamine (MDEA)
diglycolamine Tertiary Amino Azabicyclic Alcohols endo-8-methyl-8-azabicyclo [3,2,1] octan-3-ol (tropine)
N-hydroxyethyl-9-azabicyclo [3,3,1] nonane
3-hydroxymethyl-8-methyl-8-azabicyclo [3,2,1] octane
etc Sterically Hindered Amines 2-amino-2methyl-1-propanol
2-amino-2-methyl propionic acid
2-amino-2-phenyl propionic acid
pipecolinic acid
4,8-p-menthane diamine etc.

Combination physical/chemical solvent systems, typically containing at least one physical and one chemical solvent, may include:

TABLE (i) methanol-diglycol amine- as is used in the Amisol system;
(ii) water-N-methyl diethanolamine as is used the UCARSOL HS system;
(iii) sulfolane-diisopropanolamine-water as is used in the Sulfinol system; etc.

In accordance with the practice of the process of this invention, the gas dissolved in the charge rich liquid may contain a basic gas such as ammonia or an acid gas such as carbon dioxide, hydrogen sulfide, etc. or a neutral gas such as nitrogen, oxygen, carbon monoxide, carboxyl sulfide, carbon disulfide, argon, hydrogen, methane, etc. These gases maybe present in amounts ranging from very small to very large amounts. Typically they are present in the equilibrium concentration at temperature and pressure of operation.

Illustrative charge rich liquid may contain:

TABLE (i) methanol containing carbon dioxide;
(ii) N-methyl diethanolamine containing carbon dioxide;
(iii) tetraethylene glycol dimethyl ether containing carbon dioxide;
(iv) methanol containing hydrogen sulfide;
(v) N-methyl diethanolamine containing hydrogen sulfide;
(vi) tetraethylene glycol dimethyl ether containing hydrogen sulfide; etc.

The charge rich liquid containing gas dissolved in solvent may typically be at temperature of minus 100° C. - plus 50° C., preferably minus 30° C. - plus 25° C., say minus 10° C. and pressure of 0-1000 psig, preferably 0-500 psig, say 100 psig.

The gas permeable, essentially solvent-impermeable, dense skin membrane which may be used in practice of the process of this invention may be characterized by the following properties:

(i) Substantial inertness with respect to the gas and liquid components of the system;
(ii) High permeability to the gas component to be desorbed;
(iii) Low permeability to the liquid component of the rich liquor;
(iv) Structural stability under operating condition of temperature, pressure, etc.

The membranes which may be employed typically have a pore size of less than about 1000 A, preferably about 0-100, say 11 A, a thickness of about 0.0005-0.005 inches, (i.e. 0.5-5 mils) and a permeability to standard carbon dioxide gas at 25° C./14.7 psig of $1 \times 10^{-7}$ to $1 \times 10^{-2}$ cc/sec cm$^2$cm Hg.

These membranes typically have a molecular weight cutoff of below about 1000 and commonly in the range of about 0-200 or even less—say below about 100 i.e. materials of molecular weight greater than this are essentially not passed through the membrane. The molecular weight cutoff should be as low as possible. The membranes which may be employed may include:

TABLE (i) Polytetrafluoroethylene membranes (typified by the Gore Tex membranes of W. L. Gore and Associates) which may be used on a laminated substrate of polyethylene, polypropylene, polyester, polyurethane, etc. These membranes may have a pore size of about 0.01-20 millimicrons (i.e. about 0.1-200 A), a thickness of about 0.5-5 mils, and a porosity of about 50-98%.

A specific Teflon membrane may be the Gore Tex membrane of 1 millimicron (10° A) pore size and 0.003 inch (3 mil) thickness. This membrane has typical porosity of about 91%.

(ii) Cellulose Acetate membranes (typified by the SEPA membranes of Osmonics Inc.) which may be anisotropic membranes having a dense skin on top of a porous support layer. These membranes may have a pore size of 4-20 A and a molecular weight cutoff of as low as 200 (or less).

A specific membrane may be the SEPA-50 cellulose acetate membrane which is characterized by a molecular weight cut off of about 600 for organics, and a pore size of about 11 A. Maximum suggested pressure employed may be 300 psig and the flux at recommended pressure of 200 psig may be $1.36-2.72 \times 10^{-3}$ cc/sec cm$^2$.

Another specific membrane may be the SEPA-99 cellulose acetate membrane which is characterized by a molecular weight cutoff of less than 200 for organics, and a pore size of about 4 A.

The flux at 800 psig may be $0.39-1.17 \times 10^{-3}$ cc/sec cm$^2$.

(iii) Polyethylene imine membranes (typified by the SEPA membranes of Osmonics Inc) which may be anisotropic membranes having a dense skin on top of a porous support layer. These membranes may have pore size of below about 1000 A and a molecular weight cutoff as low as 200 (or less).

A specific membrane may be the SEPA-50 polyethylene imine membrane which is characterized by a molecular weight cutoff of about 600 for organics and a pore size of about 11 A. Maximum suggested pressure employed may be 300 psig and the flux at recommended pressure of 200 psig may be, $1.35-2.72 \times 10^{-3}$ cc/sec cm$^2$.

(iv) Hydrolyzed Cellulose membranes (typified by the SEPA membrane of Osmonics Inc.) which may be anisotropic membranes having a dense skin on top of a porous support layer. These membranes may have a pore size of about 10 A and a molecular weight cutoff of about 500.

A specific membrane may be the SEPA 50 HC hydrolyzed cellulose membrane which is characterized by a molecular weight cutoff of about 600 for organics, and a pore size of about 10 A. Maximum suggested pressure employed may be 500 psig and the flux at recommended pressure may be as high as $6-7 \times 10^{-3}$ cc/sec cm$^2$.

It will be apparent that the best membrane for use in a particular system will depend on the composition of the liquid-gas charge, the inertness of the membrane to the chemical and physical composition of the gas liquid charge, and the flux attainable when treating a particular charge.

Preferably the membrane is supported on a structure which may include closely space members, a screen, a more porous membrane, etc. In practice, the membrane is mounted in a wall which is common to an inlet chamber and a outlet chamber. Charge rich liquid in liquid phase containing gas dissolved in solvent is admitted through an inlet conduit into the inlet chamber and maintained therein at operating temperature and pressure. The charge rich liquid is maintained in contact with the membrane and, under the influence of the pressure drop across the membrane, the gas content thereof passes through the membrane into the outlet chamber. In preferred operation, little or no liquid passes through the membrane.

The lean liquid leaves the inlet chamber through an outlet conduit. The gas collected in the outlet chamber may be withdrawn and recovered.

In a preferred embodiment, the lean liquid leaving the inlet chamber through the outlet thereof may be used as lean liquor to an absorber to which charge gas is admitted. The lean liquor absorbs the desired component (the lean gas so formed is recovered as overhead); and the rich liquid so formed may be passed to the membrane-desorption operation.

The pressure of the inlet side of the membrane may be at absorber operating pressure, typically 200–500 psig, say 500 psig. The pressure on the permeate side of the membrane may be slight vacuum, say about 10 mm. Hg, to slight pressure say 30 psig, preferably as low as can be maintained without solvent permeation. The pressure drop across the membrane may be sufficient to drive the gas through the membrane by pressure differential, typically 200–500 psig, say 500 psig.

ADVANTAGES OF THE INVENTION

It is a feature of the process of this invention that it may be characterized by the following advantages inter alia:

(i) it provides a simple technique for separating a concentrated gas stream from charge rich liquid;

(ii) it permits reduction of sensible heat requirements (energy required to raise rich solvent to reboiler temperature);

(iii) it permits reduction of the energy requirements which would be needed to vaporize components in the regenerator-stripper of an absorption system;

(iv) it minimizes losses due to solvent degradation at high temperature;

(v) it minimizes losses due to solvent vaporization;

(vi) it permits operation with high solvent circulation rates;

(vii) it permits separation of gas from liquid with lower capital costs; etc.

DESCRIPTION OF PREFERRED EMBODIMENT

Practice of the process of this invention will be apparent to those skilled in the art from the following wherein as elsewhere in this specification all parts are parts by weight unless otherwise set forth.

EXAMPLE I

In this Example which represents the best mode presently known of practicing the process of this invention, there is admitted as lean liquor to the top of a packed bed absorption tower, tetraglyme (i.e. the dimethyl ether of tetraethylene glycol) at 500 psig and minus 12° C. There is admitted to the bottom of the tower, a rich gas stream containing hydrogen sulfide.

Lean gas leaving the tower overhead contains a decreased quantity of hydrogen sulfide. Rich liquor leaving the bottom of the absorption tower contains tetraglyme and hydrogen sulfide.

The rich liquor bottoms stream at 500 psig is heated to 25° C. and passed into the inlet chamber of a membrane desorption unit which contains sheets of the Osmonic SEPA 50 HC brand of hydrolyzed cellulose membrane which has a molecular weight cutoff of approximately 600 for organics and a nominal pore size of about 10 A.

During an effective residence time at 25° C. and 500 psig in contact with the membrane, hydrogen sulfide gas passes through the membrane and tetraglyme is retained. No significant portion of tetraglyme passes through the membrane. The retentate or lean liquor may be found to contain tetraglyme and essentially no hydrogen sulfide. Permeate passing through the membrane contains hydrogen sulfide (at atmospheric pressure) and is essentially free of tetraglyme liquid. Retentate liquid, tetraglyme, may be passed to the absorber as lean liquor. Permeate pressure is atmospheric.

EXAMPLE II

In this Example, tetraglyme liquid, saturated with carbon dioxide at 500 psig and 25° C., is passed into contact with the membrane of Example I at 500 psig and 25° C. The carbon dioxide flux is $6.5 \times 10^{-3}$ cc/sec cm$^2$. No liquid passes through the membrane with the gas permeate.

EXAMPLE III

In this Example, the procedure of Example II is followed, except that the absorber pressure is 300 psig and the pressure in the membrane desorber-stripper is 270 psig. The flux is $4.1 \times 10^{-3}$ cc/sec cm$^2$. Permeate pressure is atmospheric.

EXAMPLE IV

In this Example, the procedure of Example II is followed except that the absorber pressure is 100 psig and the pressure in the membrane desorber-stripper is 70 psig. The flux is $1.1 \times 10^{-3}$ cc/sec cm$^2$. Permeate pressure is atmospheric.

EXAMPLE V

In this Example, the procedure of Example IV is followed except that the membrane is the SEPA 99 CAB cellulose acetate membrane. The flux is $8.1 \times 10^{-5}$ cc/sec cm$^2$.

Results comparable to those attained in Example II may be attained if the charge rich liquor is as follows

TABLE

| Example | CHARGE RICH LIQUOR |
| --- | --- |
| VI | N-methyl diethanolamine containing carbon dioxide |
| VII | Methanol containing carbon dioxide |

TABLE-continued

| Example | CHARGE RICH LIQUOR |
|---------|-------------------|
| VIII | Tetraethylene glycol containing carbon dioxide |
| IX | N-formyl morpholine containing carbon dioxide |
| X | Methanol plus diglycol amine containing sulfur dioxide |

Although this invention has been illustrated by reference to specific embodiments, it will be apparent to those skilled in the art that various charges and modifications may be made which clearly fall within the scope of the invention.

What is claimed is:

1. The method of separating a charge rich liquid containing gas dissolved in solvent therefor which comprises maintaining said charge rich liquid containing gas dissolved in solvent therefore in liquid phase in contact with a gas-permeable, essentially solvent impermeable membrane of pore size of less than about 1000 A and molecular weight cutoff of below about 1,000 selected from the group consisting of cellulose acetate membrane, hydrolyzed cellulose membrane, and polyethyleneimine membrane, and;

maintaining a pressure drop across said gas-permeable essentially solvent-impermeable membrane;

passing said gas from the charge rich liquid containing gas dissolved in solvent therefore at the higher pressure side of said membrane through said membrane thereby forming lean liquid containing decreased quantities of gas dissolved in solvent on the higher pressure side of said membrane and, on the lower pressure side of said membrane, gas containing decreased quantities of liquid;

recovering lean liquid containing decreased quantities of gas dissolved in solvent from the high pressure side of said membrane; and recovering gas containing decreased quantities of liquid from the lower pressure side of said membrane.

2. The method of separating a charge rich liquid containing gas dissolved in solvent therefor as claimed in claim 1 wherein said gas is
   carbon dioxide
   hydrogen sulfide
   carbon disulfide
   hydrogen cyanide
   carbonyl sulfide
   methyl mercaptan
   sulfur dioxide or
   ammonia.

3. The method of separating a charge rich liquid containing gas dissolved in solvent therefor as claimed in claim 1 wherein said gas is hydrogen sulfide.

4. The method of separating a charge rich liquid containing gas dissolved in solvent therefor as claimed in claim 1 wherein said gas is carbon dioxide.

5. The method of separating a charge rich liquid containing gas dissolved in solvent therefor as claimed in claim 1 wherein said charge rich liquid is selected from the group consisting of alcohols, glycols, polyoxyalkylene polyols, glycol ethers, organic carbonates, nitrogen heterocycles, sulfur heterocycles, amines, and olamines.

6. The method of separating a charge rich liquid containing gas dissolved in solvent therefor as claimed in claim 1 wherein said solvent is methanol.

7. The method of separating a charge rich liquid containing gas dissolved in solvent therefor as claimed in claim 1 wherein said solvent is tetraethlene glycol dimethyl ether.

8. The method of separating a charge rich liquid containing gas dissolved in solvent therefor as claimed in claim 1 wherein said solvent is N-methyl diethanolamine.

9. The method of separating a charge rich liquid containing gas dissolved in solvent therefor as claimed in claim 1 wherein said solvent is N-formyl morpholine.

10. The method of separating a charge rich liquid containing hydrogen sulfide gas dissolved in dimethyl ether of tetraethylene glycol solvent which comprises maintaining said charge rich liquid containing hydrogen sulfide gas dissolved in dimethyl ether of tetraethylene glycol solvent in contact with a gas-permeable, essentially solvent impermeable, hydrolyzed cellulose acetate membrane of pore size of about 0.1–1000 A and molecular weight cutoff of less than about 1000;

maintaining a pressure drop across said membrane of about 200–500 psig;

passing hydrogen sulfide from the charge rich liquid containing hydrogen sulfide dissolved therein at the higher pressure side of said membrane through said membrane thereby forming lean liquid containing decreased quantities of hydrogen sulfide on the higher pressure side of said membrane and on the lower pressure side of said membrane, gas containing decreased quantities of liquid;

recovering lean liquid containing decreased quantities of hydrogen sulfide from the high pressure side of said membrane; and recovering hydrogen sulfide containing decreased quantities of liquid from the lower pressure side of said membrane.

* * * * *